US010052133B2

(12) United States Patent
Kao et al.

(10) Patent No.: US 10,052,133 B2
(45) Date of Patent: Aug. 21, 2018

(54) KIRSCHNER WIRE FIXATION STRUCTURE

(71) Applicants: Chang Gung Memorial Hospital, Linkou, Taoyuan (TW); Ming Chi University of Technology, New Taipei (TW)

(72) Inventors: Hsuan-Kai Kao, Taoyuan (TW); Chih-Chung Hu, New Taipei (TW)

(73) Assignees: CHANG GUNG MEMORIAL HOSPITAL, LINKOU, Taoyuan (TW); MING CHI UNIVERSITY OF TECHNOLOGY, New Taipei (TW)

( * ) Notice: Subject to any disclaimer, the term of this patent is extended or adjusted under 35 U.S.C. 154(b) by 0 days.

(21) Appl. No.: 15/345,956

(22) Filed: Nov. 8, 2016

(65) Prior Publication Data
US 2017/0303968 A1 Oct. 26, 2017

(30) Foreign Application Priority Data

Apr. 26, 2016 (TW) .............................. 105112926 A

(51) Int. Cl.
*A61B 17/64* (2006.01)
*A61B 17/84* (2006.01)

(52) U.S. Cl.
CPC ........ *A61B 17/6466* (2013.01); *A61B 17/848* (2013.01)

(58) Field of Classification Search
CPC ............ A61B 17/6425; A61B 17/6458; A61B 17/6475; A61B 17/6483; A61B 17/6433; A61B 17/6466; A61B 17/848; A61B 17/6416; A61B 17/8875; A61B 17/8605
USPC ...... 606/54–68, 105, 258–261, 96, 329, 324
See application file for complete search history.

(56) References Cited

U.S. PATENT DOCUMENTS

| | | | | |
|---|---|---|---|---|
| 5,891,144 | A * | 4/1999 | Mata ................... | A61B 17/6466 606/54 |
| 7,758,582 | B2 * | 7/2010 | Ferrante ............. | A61B 17/6466 606/96 |
| 8,172,840 | B2 * | 5/2012 | Murner ............... | A61B 17/6466 403/289 |
| 9,273,715 | B2 * | 3/2016 | Bordeaux ................ | F16B 39/24 |
| 2009/0024128 | A1 * | 1/2009 | Nakamura .......... | A61B 17/6416 606/54 |
| 2012/0095462 | A1 * | 4/2012 | Miller ................ | A61B 17/6466 606/59 |

* cited by examiner

*Primary Examiner* — Pedro Philogene
(74) *Attorney, Agent, or Firm* — Guice Patents PLLC

(57) ABSTRACT

A Kirschner wire fixation structure, including: at least two joint elements, each having a plurality of through-hole passages extending in different directions; and at least one connection rod; wherein the plurality of through-hole passages of the at least two joint elements are for at least two Kirschner wires and the at least one connection rod to fit through respectively, the at least two Kirschner wires are for inserting into at least one bone, and the at least one connection rod is for connecting with the at least two joint elements to form a fixation structure outside the at least one bone to stabilize and hold the at least two Kirschner wires in place.

5 Claims, 5 Drawing Sheets

KIRSCHNER WIRE FIXATION STRUCTURE

BACKGROUND OF THE INVENTION

Field of the Invention

The present invention relates to Kirschner wires for treating bone fractures, especially to a Kirschner wire fixation structure.

Description of the Related Art

Kirschner wires (or pins) are commonly used in orthopaedic treatments for internal fixation of fractures, and generally have a length around 20 cm and a diameter ranging from 0.5 to 2 mm. Kirschner wires are suitable for treating small scale of fractures, for example, small bone fracture or avulsion fracture by piecing bone fragments thereof together. Besides, Kirschner wires can also be used for temporary fixation of fractured bones in orthopaedic surgery. In addition, to expand the applications, the diameter of Kirschner wires has become as large as 4 mm to keep bone fragments together in larger scale of fractures such as pelvic fracture or humerus fracture.

However, apart from putting on a plaster cast, there is generally no proper method to hold the inserted Kirschner wires in place and to stabilize these Kirschner wires after the surgery. The inserted Kirschner wires can be shifted out of place when impacted by external collisions or the patient's physical activities. The instability of the inserted Kirschner wires is harmful to the patients.

To solve the foregoing problem, a novel fixation structure for Kirschner wires is needed.

SUMMARY OF THE INVENTION

One objective of the present invention is to disclose a Kirschner wire fixation structure, which is capable of providing a fixation effect on at least two Kirschner wires that are inserted in at least one bone of a patient.

Another objective of the present invention is to disclose a Kirschner wire fixation structure, which is capable of providing an adjustment mechanism of three-axis freedom to facilitate the insertion of at least two Kirschner wires into at least one bone of a patient.

Yet another objective of the present invention is to disclose a Kirschner wire fixation structure, which is capable of preventing the at least two Kirschner wires that are inserted in at least one bone from being shifted out of place by external collisions or the patient's physical activities to cause harm to the patient.

For achieving the foregoing objectives, a Kirschner wire fixation structure is proposed, including:

at least two joint elements, each having a plurality of through-hole passages extending in different directions; and at least one connection rod;

wherein the plurality of through-hole passages of the at least two joint elements are for at least two Kirschner wires and the at least one connection rod to fit through respectively, the at least two Kirschner wires are for inserting into at least one bone, and the at least one connection rod is for connecting with the at least two joint elements to form a fixation structure outside the at least one bone to stabilize and hold the at least two Kirschner wires in place.

In one embodiment, each of the joint elements has a first rotational axis provided by one of the Kirschner wires, and a second rotational axis provided by one of the at least one connection rod.

In one embodiment, each of the joint elements has a male retaining base and a female retaining base, the male retaining base has a convex axle to pivotally engage with the female retaining base, and the convex axle, the first rotational axis and the second rotational axis have different extending directions respectively.

In one embodiment, the Kirschner wire fixation structure further includes a plurality of screw elements for screwing into threaded holes of each of the joint elements to compress the Kirschner wires, the at least one connection rod, and the convex axles of the joint elements.

In one embodiment, at least one of the at least one connection rod has a curved portion to match with an outline of the at least one bone.

In one embodiment, the male retaining base has a plurality of first side faces and the female retaining base has a plurality of second side faces, wherein at least two opposing side faces of the plurality of first side faces of the male retaining base are connected by one of the through-hole passages, and at least two opposing side faces of the plurality of second side faces of the female retaining base are connected by one of the through-hole passages.

In one embodiment, the at least one connection rod is implemented by a metal (stainless steel or titanium alloy, for example) material.

In one embodiment, the at least two joint elements are implemented by a metal (stainless steel or titanium alloy, for example) or a non-metal material.

In one embodiment, the screw elements are implemented by a metal (stainless steel or titanium alloy, for example) material.

To make it easier for our examiner to understand the objective of the invention, its structure, innovative features, and performance, we use preferred embodiments together with the accompanying drawings for the detailed description of the invention.

DETAILED DESCRIPTION OF THE PREFERRED EMBODIMENTS

Figure 1:
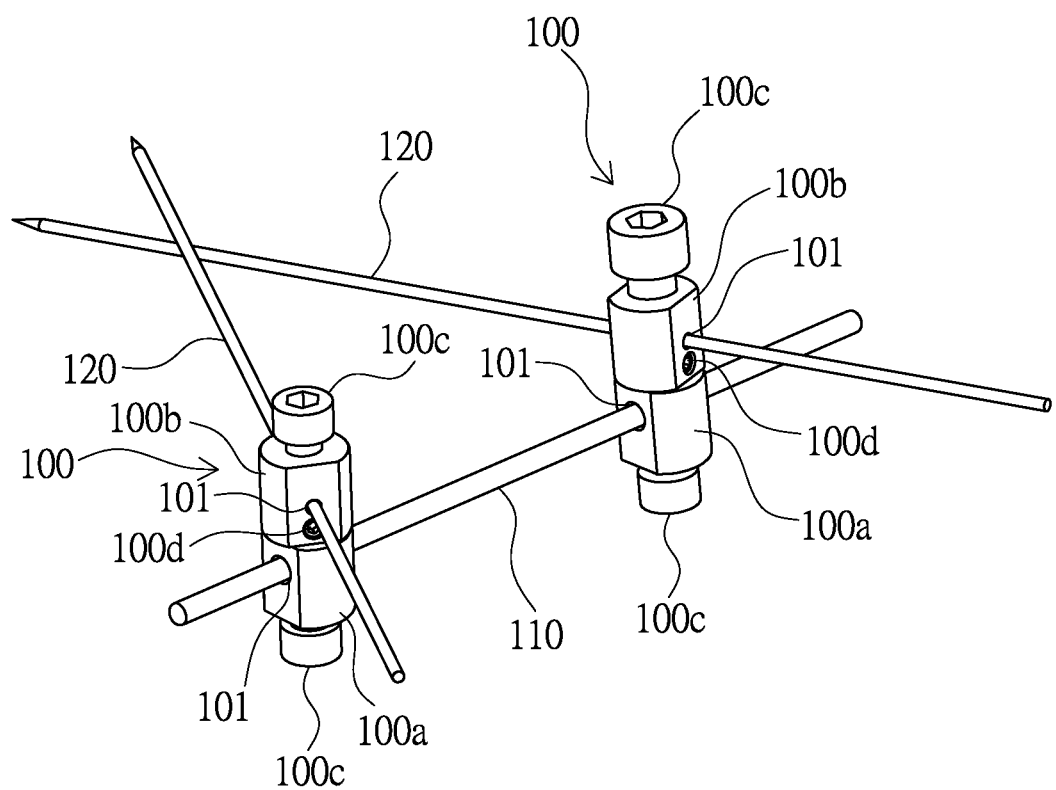
FIG. 1 illustrates an assembled diagram of a Kirschner wire fixation structure according to an embodiment of the present invention.
Figure 2:
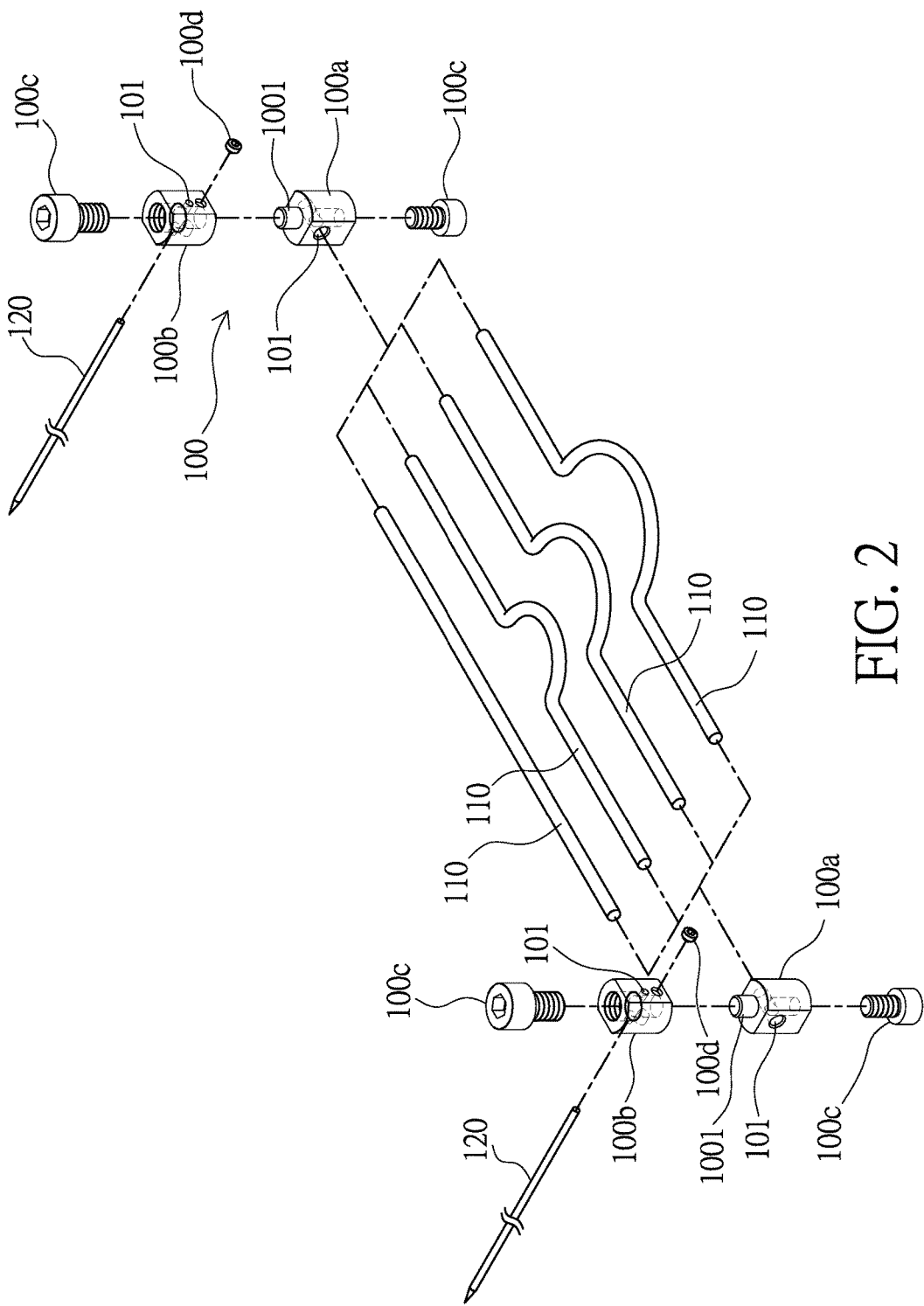
FIG. 2 illustrates an exploded diagram of a Kirschner wire fixation structure according to an embodiment of the present invention.

Please refer to FIG. 1 and FIG. 2, wherein FIG. 1 illustrates an assembled diagram of a Kirschner wire fixation structure according to an embodiment of the present invention, and FIG. 2 illustrates an exploded diagram of a Kirschner wire fixation structure according to an embodiment of the present invention. As illustrated in FIG. 1 and FIG. 2, the Kirschner wire fixation structure includes at least two joint elements 100, at least one connection rod 110, and at least two Kirschner wires 120.

The at least two joint elements 100, which can be implemented by a metal (stainless steel or titanium alloy) material, have a plurality of through-hole passages 101 extending in different directions for at least two Kirschner wires 120 and the at least one connection rod 110 to fit through respectively, wherein the at least two Kirschner wires 120 are for inserting into at least one bone, and the at least one connection rod 110 is for connecting with the at least two joint elements 100 to form a fixation structure outside the at least one bone to stabilize and hold the at least two Kirschner wires 120 in place.

Each of the joint elements 100 has a first rotational axis provided by one of the Kirschner wires 120 and a second rotational axis provided by one of the at least one connection rod 110, and includes a male retaining base 100*a*, a female retaining base 100*b*, and a plurality of screw elements 100*c*, 100*d*. The male retaining base 100*a* has a convex axle 1001 to pivotally engage with the female retaining base 100*b*, and the convex axle 1001, the first rotational axis and the second rotational axis have different extending directions respectively, wherein the extending direction of the convex axle 1001 is substantially perpendicular both to the extending direction of the first rotational axis and the extending direction of the second rotational axis.

The male retaining base 100*a* has a plurality of first side faces and the female retaining base 100*b* has a plurality of second side faces, wherein at least two opposing side faces of the plurality of first side faces of the male retaining base 100*a* are connected by one of the through-hole passages 101, and at least two opposing side faces of the plurality of second side faces of the female retaining base 100*b* are connected by one of the through-hole passages 101. By rotating the female retaining base 100*b* about the convex axle 1001, the extending direction of a through-hole passage 101 of the female retaining base 100*b* can be adjusted to a needed direction. Although only one through-hole passage 101 is illustrated in both the male retaining base 100*a* and the female retaining base 100*b* in FIG. 1, the present invention is not limited thereto, and it is to be known that both the male retaining base 100*a* and the female retaining base 100*b* can have multiple through-hole passages 101.

The screw elements 100*c*, 100*d*, which can be implemented by a metal (stainless steel or titanium alloy, for example) material, are used for screwing into threaded holes of each of the joint elements 100 to compress the Kirschner wires 120, the at least one connection rod 110, and the convex axles 1001 of the joint elements 100.

The connection rod 110, which can be implemented by a metal (stainless steel or titanium alloy, for example) material, is used to connect with two joint elements 100 and can have a curved portion to match with a bone outline, and the curved portion can have different sizes to match with different bone outlines.

Figure 3:
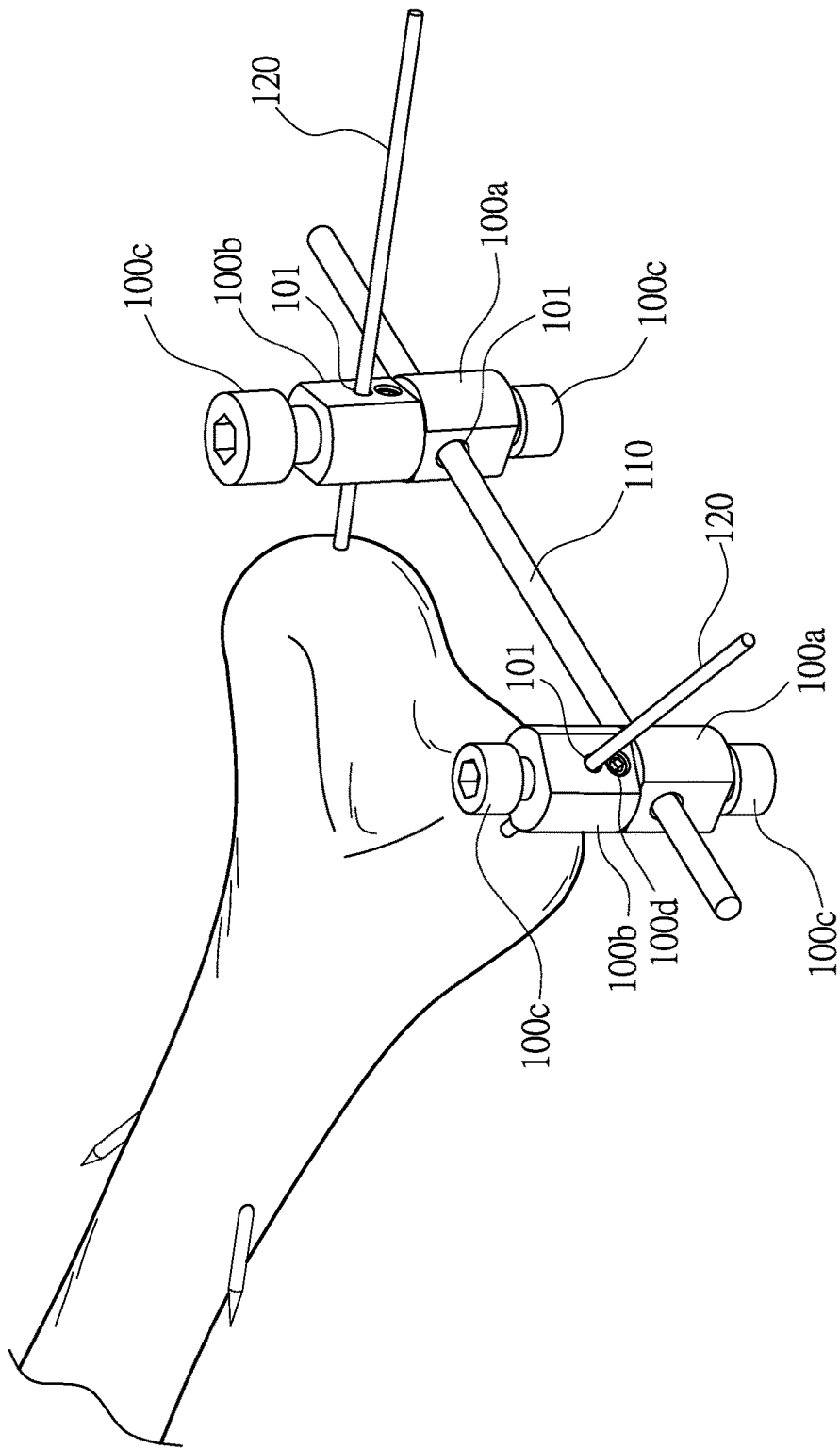
FIG. 3-5 illustrate three application scenarios of the Kirschner wire fixation structure of the present invention.
Figure 4:
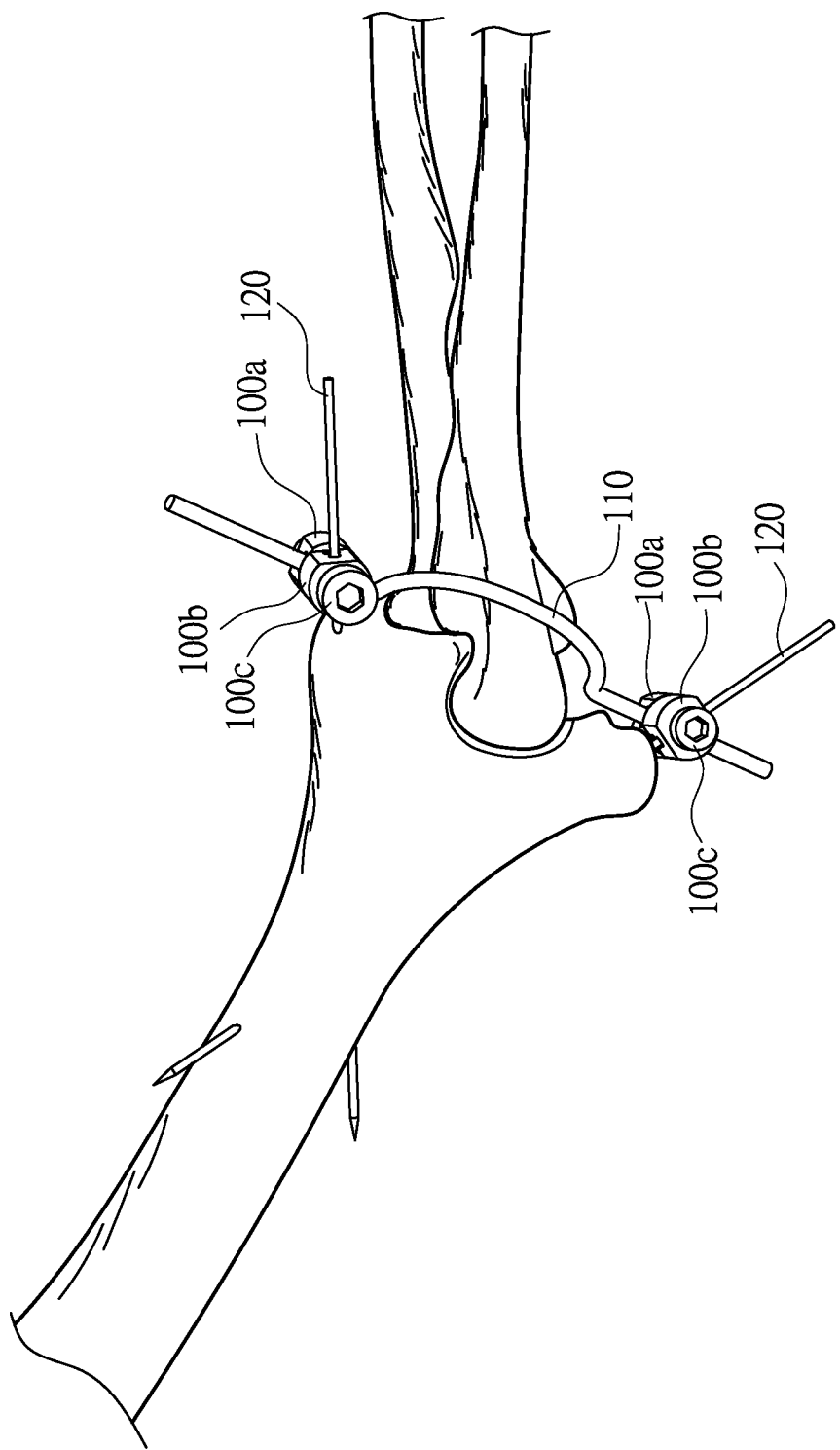
Figure 5:
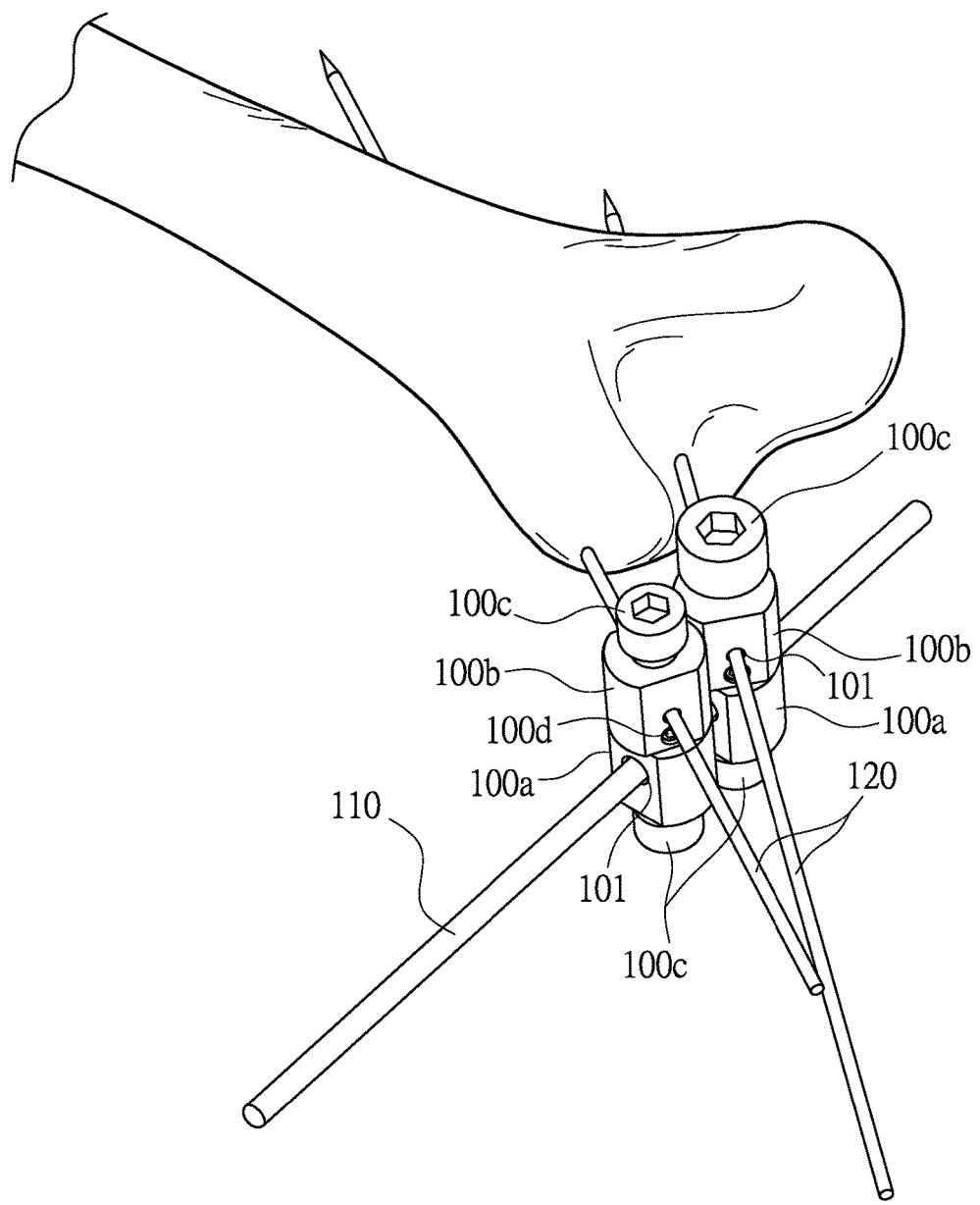

Please refer to FIG. 3-5, which illustrate three application scenarios of the Kirschner wire fixation structure of the present invention. As illustrated in FIG. 3-5, the connection rod 110 can be a straight line or have a curved portion to match with different bone outlines. In addition, a plaster cast can be put on after the Kirschner wire fixation structure of the present invention is installed.

Thanks to the designs mentioned above, the present invention can therefore offer the advantages as follows:

1. One objective of the present invention is to disclose a Kirschner wire fixation structure, which is capable of providing a fixation effect on at least two Kirschner wires that are inserted in at least one bone of a patient.

2. The Kirschner wire fixation structure of the present invention can provide an adjustment mechanism of three-axis freedom to facilitate the insertion of at least two Kirschner wires into at least one bone of a patient.

3. The Kirschner wire fixation structure of the present invention can prevent the at least two Kirschner wires that are inserted in at least one bone from being shifted out of place by external collisions or the patient's physical activities to cause harm to the patient.

While the invention has been described by way of example and in terms of preferred embodiments, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

In summation of the above description, the present invention herein enhances the performance over the conventional structure and further complies with the patent application requirements and is submitted to the Patent and Trademark Office for review and granting of the commensurate patent rights.

What is claimed is:

1. A Kirschner wire fixation structure, including:
    at least two joint elements, each having a plurality of through-hole passages extending in different directions; and
    at least one connection rod;
    wherein the plurality of through-hole passages of the at least two joint elements are for at least two Kirschner wires and the at least one connection rod to fit through respectively, the at least two Kirschner wires are for inserting into at least one bone, and the at least one connection rod is for connecting with the at least two joint elements to form a fixation structure outside the at least one bone to stabilize and hold the at least two Kirschner wires in place;
    wherein each of the joint elements has a first rotational axis provided by one of the Kirschner wires, and a second rotational axis provided by one of the at least one connection rod;
    wherein each joint element of the at least two joint elements has a male retaining base and a female retaining base, the male retaining base has a convex axle pivotally connected to the female retaining base, a screw selectively compresses the convex axle, and the convex axle, the first rotational axis and the second rotational axis have different extending directions respectively, the convex axle extends perpendicular to the first rotation axis and the second rotation axis; and
    wherein at least one of the at least one connection rod has a curved portion to match with an outline of the at least one bone;
    wherein a plurality of screw elements inserted into threaded holes of each corresponding joint element of the at least two joint elements, the plurality of screw elements directly compress the Kirschner wires and the at least one connection rod;
    wherein the plurality of screw elements and the convex axle of each joint element of the at least two joint elements share a common axis.

2. The Kirschner wire fixation structure of claim 1, wherein the male retaining base has a plurality of first side faces and the female retaining base has a plurality of second side faces, wherein at least two opposing side faces of the plurality of first side faces of the male retaining base are connected by one of the through-hole passages, and at least two opposing side faces of the plurality of second side faces of the female retaining base are connected by one of the through-hole passages.

3. The Kirschner wire fixation structure of claim 1, wherein the at least one connection rod is implemented by a metal material.

4. The Kirschner wire fixation structure of claim 1, wherein the at least two joint elements are implemented by a metal or a non-metal material.

5. The Kirschner wire fixation structure of claim 1, wherein the screw elements are implemented by a metal material.

\* \* \* \* \*